(12) United States Patent
Kanda et al.

(10) Patent No.: US 8,333,703 B2
(45) Date of Patent: Dec. 18, 2012

(54) ULTRASONIC DIAGNOSTIC APPARATUS

(75) Inventors: Hiroshi Kanda, Saitama (JP);
 Mitsuhiro Oshiki, Tokyo (JP); Ryuichi Shinomura, Saitama (JP)

(73) Assignee: Hitachi Medical Corporation, Tokyo (JP)

( * ) Notice: Subject to any disclaimer, the term of this patent is extended or adjusted under 35 U.S.C. 154(b) by 758 days.

(21) Appl. No.: 11/577,005

(22) PCT Filed: Oct. 13, 2005

(86) PCT No.: PCT/JP2005/018836
§ 371 (c)(1),
(2), (4) Date: Apr. 11, 2007

(87) PCT Pub. No.: WO2006/041114
PCT Pub. Date: Apr. 20, 2006

(65) Prior Publication Data
US 2008/0015441 A1 Jan. 17, 2008

(30) Foreign Application Priority Data
Oct. 15, 2004 (JP) .................................. 2004-300900

(51) Int. Cl.
*A61B 8/14* (2006.01)
(52) U.S. Cl. ........ 600/459; 600/437; 600/443; 367/138; 367/180
(58) Field of Classification Search .................. 600/437, 600/443, 459, 472; 367/138, 180; 73/584, 73/587, 597, 609, 618, 627, 633
See application file for complete search history.

(56) References Cited

U.S. PATENT DOCUMENTS 3,690,153 A 9/1972 Matay
4,375,166 A * 3/1983 Auphan .......................... 73/628
5,307,815 A * 5/1994 Gatzke et al. ................. 600/437
(Continued)

FOREIGN PATENT DOCUMENTS
JP 56-148056 11/1981
(Continued)

OTHER PUBLICATIONS

Johnson, J. et al., "Medical Imaging Using Capacitive Micromachined Ultrasonic Transducer Arrays", Ultrasonics, IPC Science and Technology Press Ltd. Guildford, GB, vol. 40, No. 1-8, May 1, 2002, pp. 471-476.

(Continued)

*Primary Examiner* — Brian Casler
*Assistant Examiner* — Daniel Huntley
(74) *Attorney, Agent, or Firm* — Antonelli, Terry, Stout & Kraus, LLP.

(57) ABSTRACT

An ultrasonic diagnostic apparatus is disclosed for transmitting ultrasonic waves and receiving echo signals. The apparatus includes an ultrasonic probe having transducers whose sensitivity can be controlled in accordance with bias voltage. Echo signals output from the ultrasonic probe are amplified so that an image can be constructed according to the amplified echo signals and displayed. A probe gain control device is used for controlling the bias voltage in accordance with the elapsed time from receiving the echo and matching the intensity of the echo signal output from the ultrasonic probe with the input range of a preamplifier. During a reception period while a strong echo signal is received from a superficial portion of body surface of an examinee, the reception sensitivity of the ultrasonic probe is controlled so that the echo signal level input to the preamplifier will not exceed the input range of the preamplifier.

17 Claims, 5 Drawing Sheets

U.S. PATENT DOCUMENTS

| | | | |
|---|---|---|---|
| 5,629,578 | A | 5/1997 | Winzer et al. |
| 5,889,194 | A | 3/1999 | Adams |
| 6,246,158 | B1 | 6/2001 | Ladabaum |
| 6,726,626 | B1 | 4/2004 | Hossack |
| 6,795,374 | B2 | 9/2004 | Barnes |
| 2003/0048698 | A1 | 3/2003 | Barnes et al. |
| 2003/0139664 | A1 | 7/2003 | Hunt et al. |
| 2004/0002652 | A1* | 1/2004 | Phelps et al. ............ 600/437 |
| 2004/0102704 | A1* | 5/2004 | Tsujita et al. ............ 600/443 |
| 2004/0210137 | A1* | 10/2004 | Baba et al. ............ 600/443 |
| 2005/0203392 | A1* | 9/2005 | Peteresen et al. ............ 600/437 |

FOREIGN PATENT DOCUMENTS

| | | |
|---|---|---|
| JP | 2004-008684 | 1/2004 |
| WO | WO 00/30543 A1 | 6/2000 |
| WO | WO 03/001843 A2 | 1/2003 |

OTHER PUBLICATIONS

European Search Report, dated Dec. 22, 2010, issued in corresponding European Patent Application No. 05 79 3173.

Japanese Office Action, dated Mar. 29, 2011, issued in corresponding Japanese Patent Application No. 2006-540961.

* cited by examiner

ULTRASONIC DIAGNOSTIC APPARATUS

TECHNICAL FIELD

The present invention relates to an ultrasonic diagnostic apparatus, in particular to a technique for rendering images as faithfully as possible using echo signals having wide dynamic range outputted from an ultrasonic probe.

BACKGROUND ART

An ultrasonic diagnostic apparatus is for receiving, by an ultrasonic probe, reflected waves (echo) formed by ultrasonic waves transmitted from the same ultrasonic probe and reflected within a living body, and constructing a tomographic image of the inside of the living body based on the outputted echo signals from the probe. Generally, echo signals have a wide dynamic range (for example, 100~120 dB). For example, while a signal from a superficial portion of a body surface exceeds 1V, a signal from a deep portion is only around several μV which is small, whereby the signal level received by the ultrasonic probe is extensive. The fact that the level of echo signals covers a wide range as mentioned above is a source of characteristics of the ultrasonic diagnostic apparatus that excels in rendering soft tissues. Consequently, in ultrasonic diagnostic apparatus, finding a way to render without diminishing a wide range of echo signal levels is a cornerstone in system designing.

Generally, while an echo received by an ultrasonic probe is converted into an electronic signal and amplified in a preamplifier, the scope of the upper and lower limit of the signal level possible to input to the preamplifier (hereinafter abbreviated as an input range) is specified. Therefore, for example, in the case that echo signals exceeding the input range such as the echo signals from superficial portion of the body surface like a fat layer are assumed to be inputted to the preamplifier, saturation of the preamplifier is avoided by suppressing the echo signals within the input range of the preamplifier using devices such as diode clipping circuit or diode attenuator.

On the other hand, while echo signals from a deep portion of a body tend to be attenuated and become negligible in the propagation process, the echo signals from a deep portion receive implementation for compensating the intensity by a device such as a TGC (Time Gain Control) amplifier provided with a characteristic of increasing amplification degree more on the echo signals from the deep portion than those from the shallow portion.

Patent Document 1: U.S. Pat. No. 6,246,158B1

DISCLOSURE OF THE INVENTION

Problems to be Solved

However, along with the drastic upgrade of the latest ultrasonic probes, the output level of echo signals from the probe has been improved. For example, the echo signals from a superficial portion of a body surface such as a fat layer exceeds 1.5V, which exceeds the input range of the preamplifier (for example, commonly 150 mV~500 mV) considerably. It also is a fact that the preamplifier does not have the linear amplifying characteristic in the entire input range, whereby its input range is narrowed even more in the cases such as being used for a Doppler measurement wherein nonlinearity of the preamplifier creates problems. It is therefore a significant problem to be solved, in the ultrasonic diagnostic apparatus, to match the echo signals getting higher along with the improving sensitivity of the ultrasonic probes with the input range of the preamplifier.

While matching the echo signals with the input range of the preamplifier by converting the level of the echo signals by a transformer can be an option for solving the above-mentioned problem, there are design difficulties in converting the signal level in broad spectrum by transformer, and it is also difficult to automatically adjust the size of various echo signals to be inputted.

On the other hand, the diode clipping circuit provided on the input side of the preamplifier impairs the waveform of echo signals by its clipping motion. In other words, biological acoustic information included in the waveform is impaired, which is not preferable. Similarly, as is well known, the diode attenuator provided on the input side of the preamplifier impairs S/N (signal-to-noise ratio) of the receiving system.

As has been described above, conventional art has not succeeded in downloading the echo signals having a wide dynamic range to the reception processing system or processing without impairing their waveforms. This problem has been causing another problem that the signals having a wide dynamic range cannot be imaged faithfully even though the dynamic range of echo signals has been broadened by the improvement in sensitivity of probes.

On the other hand, there is a limit to increasing the transmission power, since the limit of acoustic density within the living body is laid down by the standards of the FDA. This means that there is also a limit to increasing the intensity of the echo signals from deep portions by increasing the transmission power. Also, since reception sensitivity of ultrasonic probes is generally constant, when echo signals are attenuated in accordance with depth it is difficult to match output signals with the input range of an AD converter provided in the latter step of a device such as a generalized TGC amplifier. In order to solve this problem, it is necessary to provide a special type of TGC amplifier thus increasing the cost of the apparatus where upon the cost becomes problematic.

The objective of the present invention is to enable the rendering of the echo signals having a wide dynamic range as an image that is higher in fidelity.

Means to Solve the Problems

In order to solve the above-mentioned problems, the present invention has a fundamental feature capable of matching echo signals outputted from an ultrasonic probe with the input range of the preamplifier by using the ultrasonic probe formed by the transducers capable of controlling the detection ability according to bias voltage and by variably controlling bias voltage of the transducers thereof.

In other words, the present invention uses an ultrasonic probe having transducers capable of temporally and variably changing the transmission/reception sensitivity during transmission/reception, and changes the sensitivity of the ultrasonic probe during the transmission or reception. Particularly, during reception, it controls reception sensitivity of the probe through attenuation in the time dimension where strong echo signals from superficial portions of body surface reach the ultrasonic probe, so that the echo signal would not exceeds the input range of the preamplifier. On the other hand, in the time dimension where faint signals from deep portions of the subject can be obtained, reception sensitivity of the ultrasonic probe is enhanced. Accordingly, it is possible to provide an ultrasonic diagnostic apparatus capable of rendering an ultrasonic image drastically improved in dynamic range by enhancing the faint reflected signals from the deep portion, or without attenuating or clipping strong reflected signals from the superficial portion of a body surface.

Here, as for the transducers capable of controlling the sensitivity according to the bias voltage, either electrostriction elements of which the electricity-machinery transfer characteristic changes according to the bias voltage or vibration elements referred to as cMUT (Capacitive Micromachined Ultrasonic Transducers) can be used. While these sensitivity-variable transducers can change both transmission sensitivity and reception sensitivity, embodiments for variably changing reception sensitivity will be mainly described in detail in the present invention.

The concrete probe gain-control means of the present invention is characterized in that the intensity of the echo signals are adapted to the input range of the preamplifier by variably controlling a bias voltage for applying to an ultrasonic probe in accordance with the passage of reception time upon receiving echo signals outputted from the ultrasonic probe. In particular, it is characterized in having a time period, upon receiving echo signals, for gradually increasing the bias voltage in compliance with the passage of receiving time. The echo signals from a superficial portion of a subject are inputted at the same instant as starting the reception and the signal level is high, on the contrary the echo signals from organs in deep portion are inputted behind the starting time of reception and the signal level is small. Given this factor, the present invention sets the reception sensitivity of the probe relatively low that is to set the bias voltage low at the time of starting the reception, and increase the reception sensitivity of the probe relatively and sequentially higher in compliance with the passage of reception time that is to gradually increase the bias voltage. Accordingly, the present invention makes it possible to control the echo signals being inputted to the preamplifier within the input range of the preamplifier.

As described above, in accordance with the present invention, since the level of echo signal are controlled through controlling reception sensitivity of the ultrasonic probe, the level of echo signals can be controlled within the input range of the preamplifier without impairing the trait of waveform of the echo signals.

Also, the present invention is capable, with respect to the bias voltage upon transmission, of lowering the bias voltage at the time of starting reception, and gradually increasing it afterwards. Or, probe gain control means is capable of gradually increasing the bias voltage from the reception starting time, and maintaining the bias voltage at a set value after the passage of set time.

With such configuration, according to an embodiment of the present invention, it is possible to provide an ultrasonic diagnostic apparatus capable of acquiring an image with drastically broadened dynamic range from superficial to deep portions of a subject comparing to conventional apparatuses, by enabling the elimination of saturation in a preamplifier upon receiving the echo signals from the superficial portion of a subject, as well as enabling the enhancement of the signals from deep potions. This makes it possible to construct an image of soft tissues without impairing the trait of signals even from deep portions.

In the case the present invention is applied to an ultrasonic diagnostic apparatus comprising:

an ultrasonic probe for transmitting/receiving ultrasonic waves;

a preamplifier for amplifying echo signals outputted from the ultrasonic probe;

a time gain variable amplifier for variably changing and amplifying the gain in time axis direction of the echo signals amplified by the preamplifier;

an A/D converter for converting the echo signals amplified by the time gain variable amplifier into digital signals;

signal processing means for performing phasing addition on the echo signals converted into digital signals by the A/D converter;

image processing means for constructing an image based on the echo signals processed by the signal processing means; and display means for displaying the image constructed by the image processing means, it can be configured as below.

More specifically, the ultrasonic diagnostic apparatus can be configured comprising:

probe gain control means configured having transducers capable of variably controlling sensitivity in accordance with the bias voltage applied as the ultrasonic probe, and matching intensity of the echo signal with input range of the preamplifier by controlling the bias voltage in compliance with the elapse of reception time when receiving the echo signal; and time gain control means for variably controlling the gain of the time gain variable amplifier so as to match the echo signal outputted from the preamplifier with input range of the A/D converter.

Furthermore, the ultrasonic diagnostic apparatus can be configured comprising digital-gain control means for variably controlling the gain of the signal processing means and/ or the image constructing means so as to match the echo signal outputted from the image constructing means with input range of the display means. Also, it can be configured comprising overall-control means for coordinating and controlling the bias control means, the time gain control means, and the digital-gain control means.

In this way, the present invention is capable of constructing a highly realistic image corresponding to the echo signal with a wide dynamic range, not only by controlling the bias voltage of an ultrasonic probe configured having transducers capable of controlling the sensitivity in accordance with the bias voltage applied and suppressing the signal level of the echo signal within input range of the preamplifier without impairing its waveform, but also by adjusting the level of the echo signal without impairing the waveform coordinating with the input range of the respective parts from a probe to display means that are composing signal processing means.

EFFECT OF THE INVENTION

In accordance with the present invention, it is possible to render echo signals having a wide dynamic range as a faithfully visualized image.

BRIEF DESCRIPTION OF THE DIAGRAMS

DESCRIPTION OF THE SYMBOLS

1 . . . ultrasonic diagnostic apparatus, 10 . . . ultrasonic probe, 40 . . . pre-amplification unit, 50 . . . TGC amplification unit, 60 . . . A/D converting unit, 70 . . . digital phasing addition unit, 80 . . . image calculation constructing unit, 90 . . . display unit, 110 . . . probe gain control unit, 150 . . . TGC gain control unit, 170 . . . digital gain control unit, 200 . . . system-gain control unit, 300 . . . system control unit.

BEST MODE FOR CARRYING OUT THE INVENTION

Hereinafter, the present invention will be described based on an embodiment.
(An Embodiment of the Ultrasonic Diagnostic Apparatus)

Figure 1:
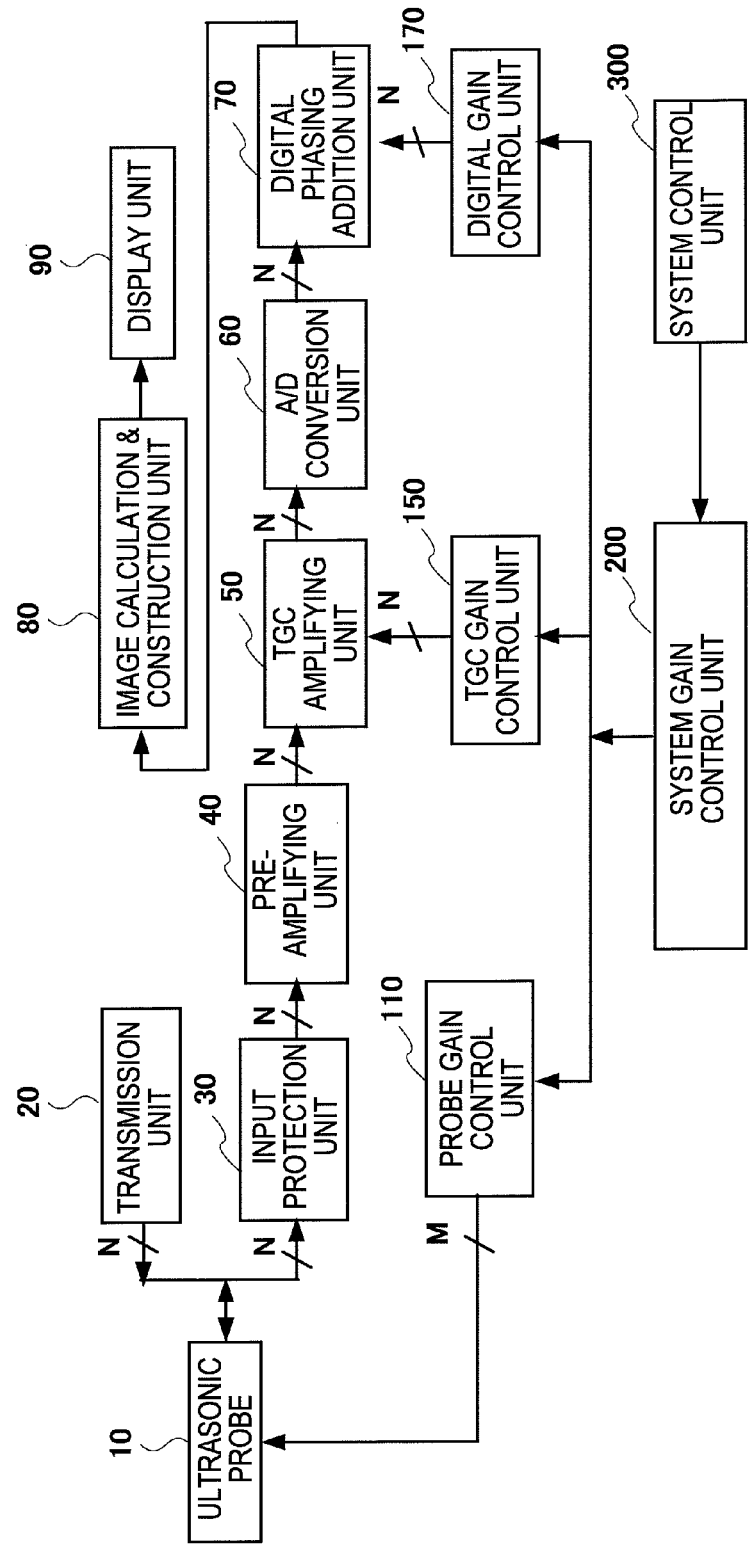
FIG. 1 is a block diagram of one embodiment of an ultrasonic diagnostic apparatus in the present invention.

FIG. 1 is a block diagram showing the configuration of an embodiment in the ultrasonic diagnostic apparatus to which the present invention is applied. The present embodiment is of an ultrasonic diagnostic apparatus capable of covering echo signals having drastically wide dynamic range than before, by using an ultrasonic probe configured with the arrangement of a plurality of transducers capable of controlling sensitivity in accordance with the value of DC bias voltage (hereinafter, described as merely a bias voltage), and temporally varying the bias voltage value during the transmission/reception.

In FIG. 1, ultrasonic probe 10 is configured with the arrangement of a plurality of transducers (element number M) capable of controlling sensitivity in accordance with the bias voltage. The transmission pulse of ultrasonic waves that respectively drives the plurality of transducers of ultrasonic probe 10 is provided from transmission unit 20. Also, the echoes received respectively by the plurality of transducers of ultrasonic probe 10 are converted into electronic signals (echo signals) and inputted to pre-amplification unit 40 via input protection unit 30. The echo signals outputted from pre-amplification unit 40 are inputted to image calculation constructing unit 80 via TGC amplification unit 50, A/D conversion unit 60 and digital phasing addition unit 70. The echo signals inputted to image calculation constructing unit 80 are converted through calculation into ultrasonic images such as B-mode, M-mode, Doppler, and color Doppler (CFM). Then the constructed respective images are displayed on display unit 90. Here, transmission unit 20, input protection unit 30, pre-amplification unit 40, TGC amplification unit 50 and A/D conversion unit 60 are configured, as is generally known, having N-number of signal processing systems corresponding to the N-number of transducers forming the transmit-receive aperture of the ultrasonic probe. In other words, one receiving system is provided to one transducer. In addition, input protection unit 30 can be omitted since it is not a circuit such as diode clipping circuit or diode attenuator for the purpose of matching the signal level with input range of pre-amplification unit 40, and is a protection circuit suitable for protecting from excessive input to a point of braking down the preamplifier, which is not a fundamental configuration requirement for the present invention.

Also, sensitivity of ultrasonic probe 10 is controlled by the bias voltage provided from probe gain control unit 110. The amplification gain of TGC amplification unit 50 is controlled by the gain provided from TGC gain control unit 150. The amplification gain of digital phasing addition unit 70 is controlled by the gain provided from digital gain control unit 170.

These probe gain control unit 110, TGC gain control unit 150 and digital gain control unit 170 are coordinated and optimally controlled by system gain control unit 200. Furthermore, system gain control unit 200 is under control of system control unit 300 for controlling the whole apparatus.

Next, the characterized portions of the present invention and configuration thereof will be described. While commonly used ultrasonic probe having transducers formed by voltage ceramics has one kind of fixed transmission/reception sensitivity based on electromechanical coupling of the voltage ceramics and geometric configuration of the transducer, the transducers for ultrasonic probe 10 of the present embodiment capable of controlling sensitivity in accordance with the bias voltage can be applied with, for example, transducers formed by electrostrictive material. This transducer using electrostrictive material takes on electricity-machine conversion, and the size of it can be controlled by intensity of the bias voltage. Also, as an example for another suitable transducer capable of controlling sensitivity by the bias voltage, a cMUT (Capacitive Micromachined Ultrasonic Transducer) can be cited. These ultrasonic probes using electrostrictive material or a cMUT have a fixed sensitivity depending on the applied bias voltage, whereby the sensitivity of the probe can be temporally varied by temporally changing the bias voltage. However, the ultrasonic probe of the present invention is not limited to the examples described above, and the point is to use the transducers capable of controlling sensitivity by bias voltage.

Here, dynamic range of the respective portions in the ultrasonic diagnostic apparatus will be described. An example of dynamic range of the respective portions using an ultrasonic probe having constant sensitivity is illustrated as a pattern diagram in FIG. 2, and dynamic range of the respective portions in the case of using an ultrasonic probe capable of variably controlling sensitivity relating to the present invention is illustrated as a pattern diagram in FIG. 3. In these diagrams, the vertical axis represents the signal level or probe sensitivity, and the horizontal axis represents the depth in a living body. Also, in these diagrams, the transmission signal for driving the ultrasonic probe is set as 100V (volts), and sensitivity of the ultrasonic probe is set as −40 dB. It also is assumed, while taking an example of a subject having standard proportions, that 1V of echo signal can be obtained immediately after the transmission at the depth of 0 cm, and around 100 μV of echo signal can be obtained from the depth of 20 cm as shown in line 1a of FIGS. 2 and 3. Also, the frequency of the ultrasonic wave used in the diagrams is set as 4 MHz, the attenuation in the living body is set at the value of an organ such as liver which is 0.5 dB/MHz/cm, and the echo signal from depth of 20 cm is set to be attenuated 0.5 dB*4 (MHz)*40 (cm: round trip)=80 dB.

Figure 2:
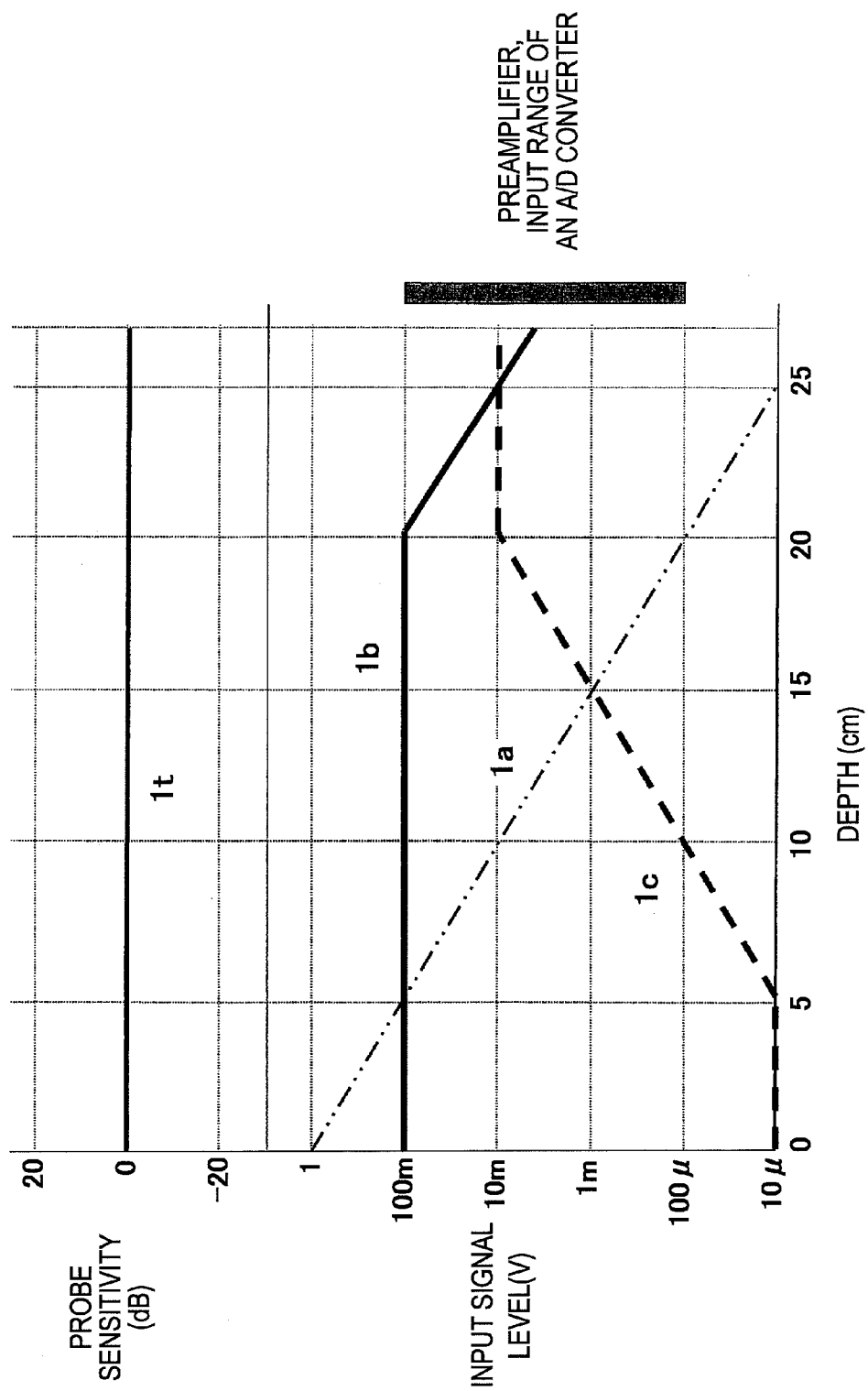
FIG. 2 is a simulated diagram of a dynamic range in the respective units of an ultrasonic diagnostic apparatus in the case of using an ultrasonic probe having constant sensitivity.

In the case of an ultrasonic probe having the transducers using the conventional voltage ceramic, the sensitivity of the ultrasonic probe is constant throughout the entire period of transmission/reception as shown in line it of FIG. 2. And the echo signal inputted to the preamplifier provided in the conventional apparatus configuration exceeds 100 mV which is the input range of the preamplifier upon reception time at the depth of 0 cm~5 cm as shown in 1a of FIG. 2. In this case, the input signal level is regulated to 100 mV (milli volts) in order to avoid the saturation of the preamplifier by providing a clipping circuit in the input unit of the preamplifier. As a result, the input signal level of the preamplifier at the depth of 0~5 cm is suppressed to 100 mV as shown in line 1b of FIG. 2. Also, while the input signal level is within the input range of the amplifier at the depth beyond 5 cm, a TGC amplifier wherein the gain increases at the depth direction is applied in order to match the signal level with the input range (for example, set as 100 mV~100 µV:60 db, 10 bits) of an A/D converter for signal-sampling. For example, this TGC amplifier has the gain characteristic that the gain increases linearly in depth direction between depths from 5 cm to 20 cm as shown in line 1c of FIG. 2. By passing through the TGC amplifier having such characteristic, echo signal 1a up to the depth of 20 cm is matched with maximum input 100 mV of A/D converter as shown in line 1b of FIG. 2. In this regard, however, since the maximum gain of the TGC amplifier is around 60 dB, the compensation by the TGC amplifier at the depth beyond 20 cm cannot be implemented. Therefore, the output power of the TGC amplifier declines to the maximum input 100 mV and below of the A/D converter at the depth beyond 20 cm as shown in line 1b of FIG. 2. If an image is constructed and displayed based on the output power of this TGC amplifier, the image of the region at the depth beyond 20 cm turns out dark. Given this factor, the amplification is performed in digital in a unit such as the latter step of the digital phasing unit for processing the signal sampled in the A/D conversion unit. However, the amplification performed in a unit such as the digital phasing unit amplifies not only the signals but also the noise level determined by input conversion noise of the preamplifier.

Figure 3:
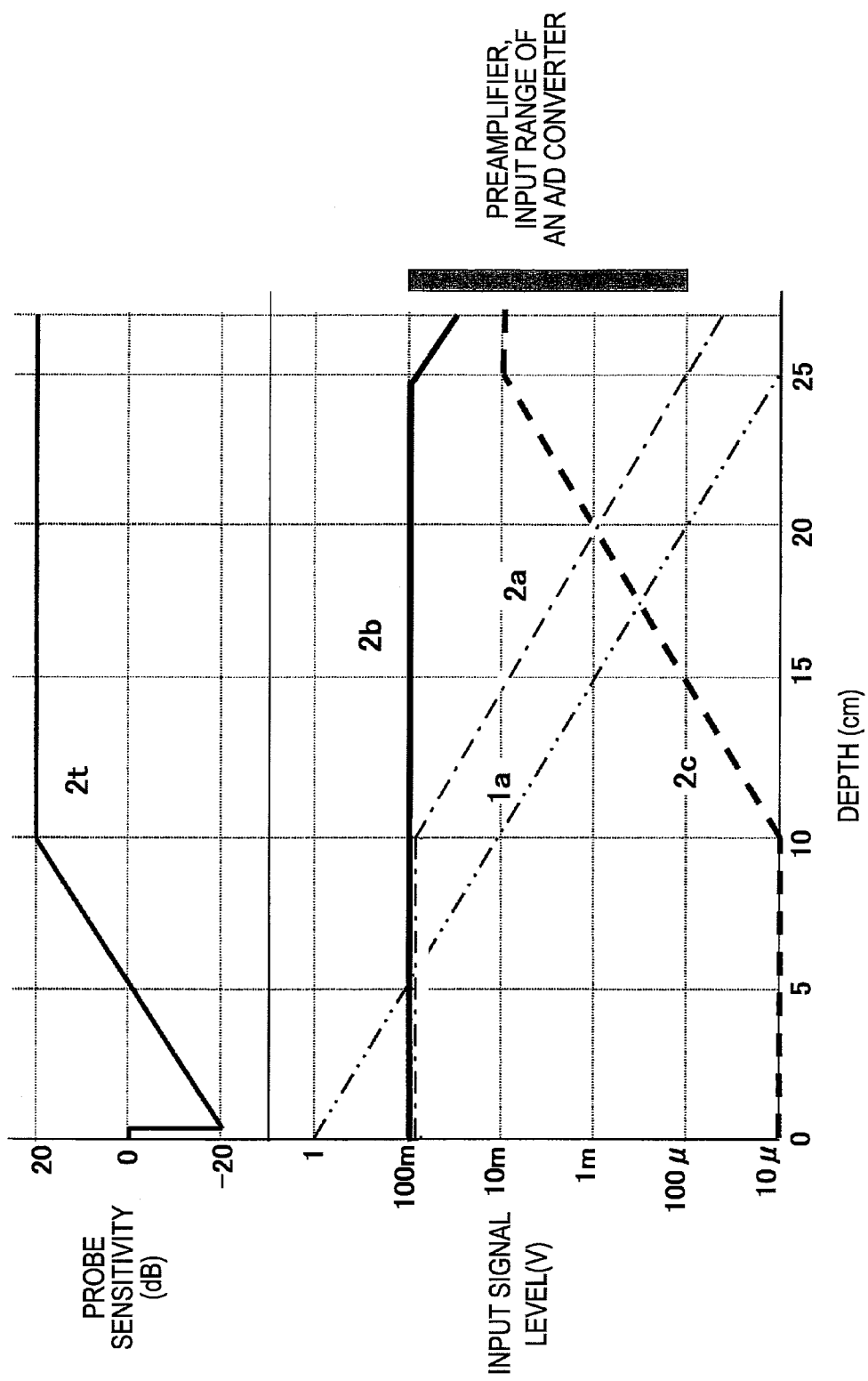
FIG. 3 is simulated diagram showing dynamic range of the respective units of an ultrasonic diagnostic apparatus relating to the present invention in the case of using an ultrasonic probe having variable sensitivity.

On the other hand, in the case of the present invention using the ultrasonic probe having transducers capable of varying the sensitivity by the bias voltage, as shown in FIG. 3 for example, when receiving the echo signal at the depth of 0~10 cm the bias voltage is changed in compliance with the passage of receiving time. More specifically, during the receiving period of the echo at the depth of 0~5 cm which exceeds the input range of the preamplifier, the input signal level of the echo signal to the preamplifier is suppressed to 100 mV which is the upper limit of the input range of the preamplifier by controlling the bias voltage. And in the following period that is the receiving period of the echo at the depth of 5~10 cm, the input signal level of the echo signal to the preamplifier is increased to 100 mV which is the upper limit of the input range of the preamplifier by controlling the bias voltage. An example of control of such reception sensitivity will be described. As shown in line 2t of FIG. 3, the reception sensitivity of the ultrasonic probe is once lowered from the transmission sensitivity (for example, 0 dB as in FIG. 2) to −20 dB at the same time of starting reception, then the reception sensitivity of the ultrasonic probe is increased in the range of 40 dB which is from −20 dB to 20 dB at the depth direction in compliance with the receiving operation of the echo signal from 0~10 cm of the subject. In the example of FIG. 3, the reception sensitivity of the ultrasonic probe with respect to the echo signal at the depth beyond 10 cm is kept constant at 20 dB. In addition, though not shown in the diagram, upon the next transmission the sensitivity of the ultrasonic probe is returned back to the original transmission sensitivity (for example, to 0 dB), thereafter the above-mentioned control is repeated in transmission/reception cycle. While the sensitivity of the ultrasonic probe is changed linearly from −20 dB to 20 dB at the echo depth of 0~10 cm in FIG. 3 illustrating the present embodiment, the change can also be represented by a curve.

As has been described above, while the signal of 1V is inputted to the pre-amplification unit in the superficial portion of a body surface when the conventional apparatus of which reception sensitivity of the probe is constantly 0 dB is used, the embodiment of the present invention controls the reception sensitivity upon starting reception to be increased from −20 dB to 20 dB whereby the input signal level to the pre-amplification unit is lowered to 100 mV which is the upper limit for suitable input range of the pre-amplification unit at the echo depth of 0~5 cm as shown in the dotted-chain line 2a of FIG. 2. Also at the echo depth of 5~10 cm, the input signal level to the pre-amplification unit is increased to 100 mV which is the upper limit for suitable input range of the pre-amplification unit. In this way, at the depth of 0~5 cm, the echo signal holding the acoustic information of the living body is increased by the preamplifier without impairing of the waveform of the echo signal, since the signal intensity is controlled within the input range of the preamplifier by reducing the echo signal level in compliance with the reception sensitivity of the probe.

Also in the embodiment of the present invention as shown in FIG. 3, when receiving the echo signal at the depth of 5~10 cm, there is no need to perform gain compensation using the TGC amplifier on the echo signal of the time region corresponding to the depth as in the conventional apparatus, since the echo signal inputted to the preamplifier is increased by increasing the reception sensitivity of the ultrasonic probe. As a result, the finite variable gain width (for example, 60 dB) of the TGC amplifier can be applied by shifting to a depth beyond 10 cm as shown in line 2c of FIG. 3. Also, when the signal level of line 1a of FIG. 2 and the signal level of line 2a of FIG. 3 are compared, the increase of signal level by 20 dB at a depth beyond 10 cm in the present embodiment can be recognized since the reception sensitivity of the ultrasonic probe increased depths of 10 cm and beyond are maintained. Therefore, in accordance with the example of FIG. 3, the region at the depth direction that can be adapted to the input range of the A/D converter can be extended by 5 cm in comparison with FIG. 2. In other words, in the case of FIG. 3, compared to FIG. 2, the echo signal in depths of up to not only 20 cm but to 25 cm can be adapted to the input range of the A/D converter, whereby the ultrasonic image with considerably wide dynamic range extending over 20 dB can be constructed in accordance with the example in the diagram. Meanwhile in the example of FIG. 3, as for depths beyond 25 cm, the signal density underruns input range of the A/D converter, thus it is necessary to control amplification degree by gain control in the digital phase unit as in the conventional manner.

Next, configuration and operation of probe gain control unit 110, TGC gain control unit 150, digital gain control unit 170 and system gain control unit 200 in FIG. 1 for carrying out gain control as shown in FIG. 3 will be described.

Probe gain control unit 110 provides the bias voltage that temporally varies to ultrasonic probe 10, and varies the sensitivity upon transmission and reception as shown in line 2t of FIG. 3. Though relationship between the bias voltage and sensitivity of the ultrasonic probe is not always linear, the reference look-up table that prescribes relationship between the bias voltage and probe sensitivity is provided in probe gain control unit 110.

TGC gain control unit 150 is for providing TGC amplification unit gain control analogue signal to the gain control terminal of TGC amplification unit 50 corresponding to the respective transducers.

Digital gain control unit 170 controls the gain of the digital amplification unit that compensates the attenuation of the signal level at the depth beyond 25 cm shown in line 2b in FIG. 2. This digital amplification unit is included in the function of digital phasing addition unit 70 as is commonly known.

These three gain control units are for outputting analogue control signals to the respective transducers of probe 10, pre-amplification unit 40 corresponding to the respective transducers and TGC amplification unit 50 corresponding to the respective transducers based on the command of digital signals provided from system gain control unit 200 controlled by system control unit 300, as well as outputting the amplification control command to digital phasing addition unit 70. Therefore, probe gain control unit 110 performs D/A conversion on each of the command of digital signals with respect to M-number of transducers provided from system gain control unit 200, and outputs the bias voltage of analogue signals to the bias circuit of the respective M-number of transducers. Also, TGC gain control unit 150 respectively performs D/A conversion on the amplification command of digital signals at the depth direction (time axis direction) with respect to the echo signal of N-number of transducers provided from system gain control unit 200, and respectively outputs the amplification command of analogue signals to N-number of TGC amplification units 50. Also, digital gain control unit 170 is for receiving the amplification command with respect to the echo signal of N-number of transducers from system gain control unit 200, and for amplifying the echo signals beyond the set depth. In this way, system gain control unit 200 optimizes the dynamic range of the system by providing control digital signals to the three gain control units.

Concrete mechanism of action for system gain control unit 200 will be described next. First, with respect to probe gain control unit 110, (1) the bias voltage for providing the reference sensitivity is induced to be applied during the transmission period of ultrasonic probe 10, (2) when entering the reception period, the lowest reception sensitivity prescribed by the kind of the transducers of ultrasonic probe 10 (−20 dB in the example of FIG. 3) is set so that the strong echo signal from a superficial portion of a body surface such as fat layer matches with the input range of pre-amplification unit 40 (100 mV in the example of FIG. 3), (3) a gradient of a DC bias for providing from the minimum reception sensitivity to the maximum reception sensitivity of ultrasonic probe 10 (the gradient of line 2*t* at depths of 0~10 cm in the example of FIG. 3) is set, and (4) DC bias for providing the maximum sensitivity is controlled to maintain constant until the next transmission.

For example, in the case of a liver, attenuation gradient in the body occurs at 4 MHz of transmission frequency and 20 dB/5 cm of gradient, the reception sensitivity is set to increase at 20 dB/5 cm of gradient.

Next, with respect to TGC amplifying unit 50, (1) the gain of TGC amplifying unit 50 is temporally increased at a gradient prescribed by the object and transmission frequency (20 dB/5 cm in the example of FIG. 3) when reached to the time the maximum reception sensitivity of the probe is imparted, (2) when an output power of TGC amplifying unit 50 either matches with the input range of A/D converting unit 60 or reaches the maximum gain of TGC amplifying unit 50, amplification degree of TGC amplifying unit 50 is maintained at the maximum value, and (3) when entering the next transmission period, the gain of TGC amplifying unit 50 is set at the minimum value.

In addition, in the example of FIG. 3, the output power of TGC amplifying unit 50 has not reached to 100 mV that is the maximum input power of A/D converting unit 60 since the maximum gain of TGC amplifying unit 50 is set at 60 dB.

Also, with respect to digital gain control unit 170, (1) the digital gain is set at 1 up to the depth that either TGC amplifying unit 50 reaches the maximum gain or the signal level reaches the maximum input power of A/D converting unit 60 (25 cm at depth in the example of FIG. 3), and (2) the digital gain is increased at a gradient prescribed by the target region and the transmission frequency as for the echo signal beyond the depth described above (20 dB/5 cm in the example of FIG. 3).

Also, system gain control unit 200 controls probe gain control unit 110, TGC gain control unit 150 and digital gain control 170 according the above-mentioned mechanism on the basis of information provided from system control unit 300 on ultrasonic probe being used, measurement target region and the transmission frequency being used. Accordingly, by controlling sensitivity of ultrasonic probe 10 temporally that is according to the depth of the measurement region, the echo signals are controlled at the intensity matching with the input range of pre-amplifying unit 40 and A/D converting unit 60 by the most suitable combination of TGC gain control unit 150 and digital gain control unit 170. As a result, in accordance with the present embodiment, it is possible to construct an image high in fidelity corresponding to a wide dynamic range of an echo signal, since the dynamic range of the reception processing system that covers from the reception to the imaging process is drastically improved.

(An Embodiment of an Ultrasonic Probe)

Here, an embodiment of ultrasonic probe 10 being one of the keys for the present invention will be described. Ultrasonic probe 10 is an array-type capable of controlling the sensitivity of the transmission and reception by the bias voltage, and a simulated configuration of one embodiment thereof is illustrated in FIG. 4.

Figure 4:
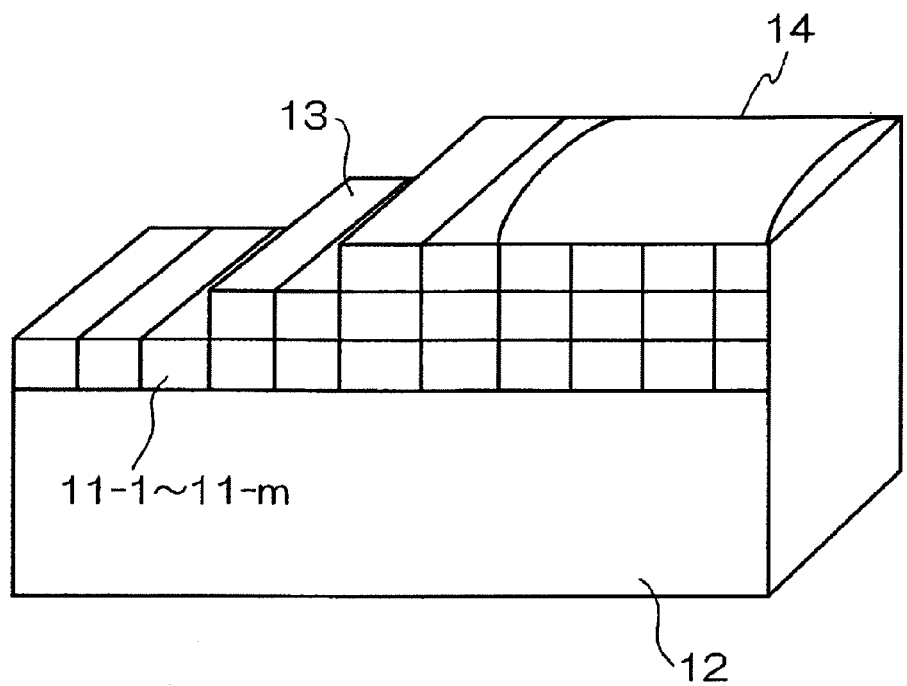
FIG. 4 is a diagram showing the configuration of one embodiment of the ultrasonic probe illustrated in FIG. 1.

Ultrasonic probe 10 of the preferred embodiment shown in FIG. 4 has the configuration of one-dimensional array in which a plurality of transducers 11-1~11-*m* (m: for example, a whole-number such as 192) is arranged in strips. Backing layer 12 is provided on the back of the array of transducers 11-1~11-*m*, matching layer 13 is arranged, for example, in two-layers on the ultrasound transmission side on the upper part of the plurality of transducers in the diagram, and acoustic lens 14 is further arranged on matching layer 13. Transducers 11-1~11-*m* transmit the transmitting electrical signals provided from transmission unit 20 to the subject by converting them into ultrasonic waves, as well as outputs the ultrasonic waves reflected in the living body after receiving them and converting them into echo signals of the electrical signals. Backing layer 12 is arranged to absorb unnecessary ultrasonic waves transmitted on the back of the transducers, as well as to constrain the unnecessary vibration of the transducers. Matching layer 13 is for improving propagation efficiency of the ultrasonic waves to the subject by matching acoustic impedance of the transducers and the subject. Also, acoustic lens 14 is for making the beams converge in the minor axis direction that is orthogonal to the array direction of the transducers.

Figure 5:
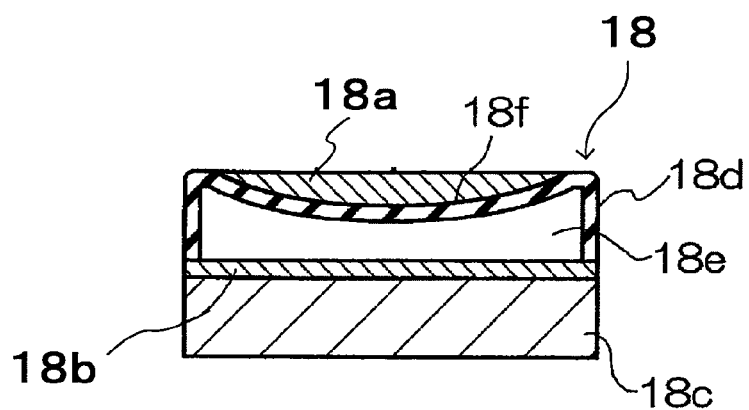
FIG. 5 is a plane view showing a detailed drawing of a transducer of the ultrasonic probe illustrated in FIG. 4.

Here, transducers 11-1~11-*m* are respectively formed by adelphus of multiple number of vibrating elements, and the respective vibrating elements have the configuration of micro-drum 18 as shown in FIG. 5. Micro-drum 18 is referred to as Capacitive Micro-fabricated Ultrasonic Transducer (cMUT) since it is manufactured using fine processing technology of semiconductor process. The respective vibrating elements are formed in hexagon in plane viewpoint. A pattern diagram of a cross-sectional configuration of a micro-drum 18 is illustrated in FIG. 5. Micro-drum 18 is configured having lower electrode 18*b* formed on silicon substrate 18*c* which is a semiconductor substrate, semiconductor thin membrane 18*f* formed on supporting portion 18*d* via supporting portion 18d made of insulating material, and upper electrode 18a further formed in upper part of semiconductor thin membrane 18f. Vacuum vacancy (gap) 18e is formed between superconductor thin membrane 18f and lower electrode 18b by etching. Semiconductor thin membrane 18f is formed by a substance such as compound semiconductor, and has the configuration of being suspended in the air and strained like a vibrating membrane of a drum, via supporting portion 18d facing lower electrode 18b.

Figure 6:
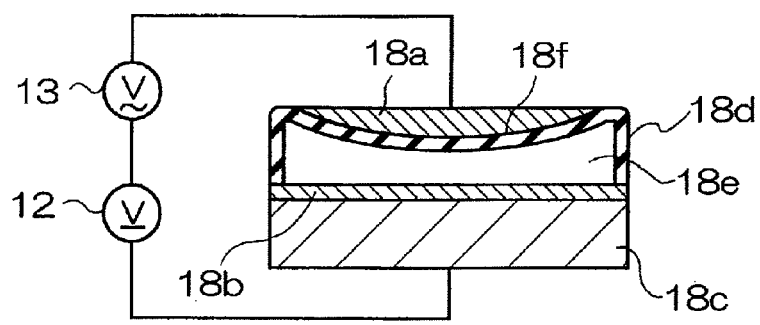
FIG. 6 is a diagram showing a cross-sectional configuration of a micro-drum in the transducer illustrated in FIG. 5.

FIG. 6 is a schematic diagram of a drive circuit of the above-mentioned cMUT. When DC bias voltage 12 is applied between upper electrode 18a and lower electrode 18b by the drive circuit shown in FIG. 6, a thin membrane of upper electrode 18a is strained with appropriate tension, being attracted to the side of lower electrode 18b by a coulomb force generated between the electrodes. Then when drive alternative current signal (a signal equivalent of a transmission pulse signal) 13 is applied between upper electrode 18a and lower electrode 18b, an ultrasonic wave is generated just as a drum of a musical instrument generates sound by being struck continuously. Also, when ultrasonic waves are inputted to micro-drum 18, the membrane vibrates in proportion to the size and waveform of the ultrasonic waves. As a result, since the capacitance value of a condenser formed by upper electrode 18a and lower electrode 18b is changed corresponding to the vibration of the membrane, the received ultrasonic waves can be converted into electrical signals by abstracting the change of capacitance value of the condenser as electrical signals.

The respective transducers 11 shown in FIG. 4 have configuration in which many of micro-drums 18 configured as shown in FIG. 5 are arranged. Upper electrode 18a and lower electrode 18b of the drug group of transducers 11 formed by arranging micro-drums 18 are respectively and mutually connected. Therefore, the respective transducers have the same function electrically as the parallel condenser in which many condensers formed by micro-drum 18 are connected in parallel.

Figure 7:
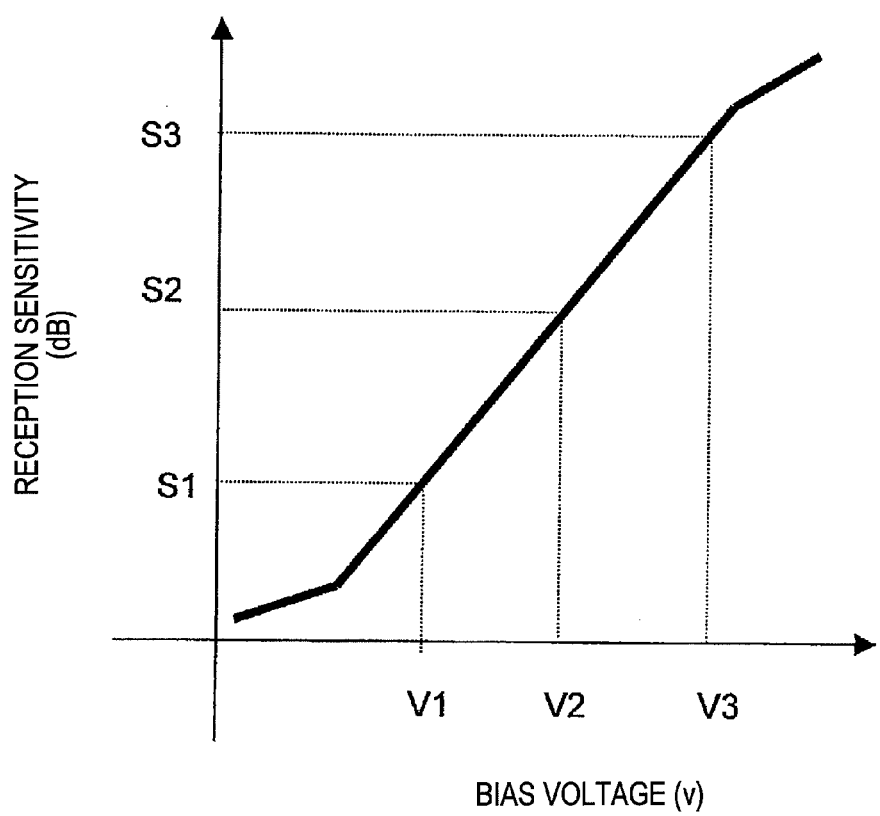
FIG. 7 is a diagram showing the bias voltage dependence of reception sensitivity in the micro-drum illustrated in FIG. 4.

Here, operation of the transducers configured having micro-drum 18 will be described in detail. It is known that sensitivity that represents electromechanical conversion efficiency of the transducers having micro-drum 18 configured as shown in FIG. 5 or FIG. 6 is non-linearly dependent on the intensity of bias voltage (Patent Document 1). Since the transducers used for an ultrasonic probe have both transmitting capability for converting electrical signals into acoustic signals and receiving capability for converting acoustic signals into electrical signals, both transmission sensitivity and reception sensitivity representing conversion efficiency thereof are non-linearly dependent on the intensity of bias voltage. An example of relationship between reception sensitivity and bias voltage is illustrated in FIG. 7. The horizontal axis of FIG. 7 represents intensity of the bias voltage and the vertical axis represents reception sensitivity, indicating the typical bias voltage dependency.

For example, in the case that gap 18e is 100 nm, the electrical signal received when bias voltage is 10V(V1), 40V (V2), and 80V(V3) corresponding to the ultrasound input of 1 kPa turn out to be 1 mV(S1), 10 mV(S2) and 100 mV(S3) as the representative values. Therefore, it is well possible to variably change sensitivity of ultrasonic probe 10 by 40 dB through controlling bias voltage 12. The reception sensitivity in FIG. 7 can be precisely controlled through obtaining a curve relation concerning other than 3 points mentioned above by interpolation and storing them in a look-up table of probe gain control unit 110. If necessary, reception sensitivity can be precisely controlled also through implementing actual measurement on relationship between the bias voltage and the reception signal, and creating the look-up table.

The transducers formed by micro-drums 18 shown in FIG. 5 are known as cMUT (Capacitive Micromachined Ultrasonic Transducers) in Document (IEEE Trans. Ultrasonics. Ferroelectric. Freq. Control Vo145, pp. 678-690, May 1998). However, in this document, there is no description of temporally (according to depth of an echo) changing DC bias voltage during transmission/reception period, that is, temporally changing the probe sensitivity as a probe TGC, which is mentioned in the present invention.

Meanwhile, it is a concern that unnecessary transmission is performed by drastically changing DC bias voltage. However, in the case that diameter of the drum is 50 microns, since resonance frequency of the micro-drum used for cMUT turns out to be around 20 MHz, it is a high-frequency outside of frequency band to use for imaging which is 1~15 MHz. Therefore, hardly any unusable acoustic transmission occurs and electrical spike waveforms are also negligible, whereby it is possible to easily remove the waveforms using an anti-aliasing filter.

While an embodiment of the present invention is described above, various changes may be made without departing from the scope of the invention. For example, though an example described in the above-mentioned embodiment is of controlling input signal level so that it is gradually increased up to reaching 10 cm of echo depth with sensitivity of the ultrasonic probe upon reception set at −20 dB at a starting time assuming that a subject has standard proportions, the subject has variety of body types such as obese or slim. Given this factor, reception sensitivity of the ultrasonic probe may be set variable according to the subject.

As for changing reception sensitivity of an ultrasonic probe according to a subject, there are several variant embodiments that are conceivable. The first variant embodiment may be for setting the specific reception sensitivity of the ultrasonic probe according to a subject by obtaining echo depth wherein the preamplifier is freed from saturated state by system control unit 300 from echo signals measured from the subject, setting reception sensitivity of the ultrasonic probe at the echo depth thereof as 0 dB, and referring to previously described −20 dB of reception sensitivity upon reception start time and 20 dB of maximum reception sensitivity. In this case, gain control of TGC amplifying unit is started from echo depth wherein reception sensitivity of the ultrasonic probe reaches to the maximum reception sensitivity, and gain control of digital phasing unit may be configured to be implemented from echo depth wherein TGC amplifying unit reaches to the maximum value.

The second variant embodiment is for changing reception sensitivity manually by an operator by referring to an ultrasonic image displayed on a monitor. In this case, an operation device for changing reception sensitivity of an ultrasonic probe is provided in a console panel of the apparatus. And it can be set so that an operator who observes an ultrasonic image displayed on a monitor can carry out the operation when he/she feels that echo depth wherein an amplifying unit is saturated is either deeper or shallower than the standard setting. As an example, when the operation device is operated in a direction that the depth where reception sensitivity of a probe being 0 dB is increased, the reception sensitivity changes so that the gradient of the probe sensitivity shown in FIG. 3 becomes more flat (gentle? smooth?) that is the position where probe sensitivity is 0 dB moves toward deeper depth direction. Contrarily, when the operator felt that the echo depth where the pre-amplifying unit being saturated is shallower than the standard setting, the operator operates the device in a reversed direction from the direction mentioned above. By doing so, reception sensitivity changes so that the position where depth sensitivity is 0 dB moves toward shallower depth direction. In this case also, software in the system control unit can be configured so that gain control of TGC amplifying unit starts from the echo depth where reception sensitivity of the probe reaches the maximum value, and gain control of the digital phasing unit is performed from the echo depth where TGC amplifying unit reaches the maximum point.

In the second embodiment, another variable is to parallel move the gradient part of ultrasonic probe sensitivity $2t$ listed in FIG. 3 to the right or left using the device. This embodiment is found to be useful for, for example, performing examination on a subject having thick subcutaneous fat. More specifically, in this varied embodiment, reception sensitivity of the probe is set at −20 dB upon reception start time of the echo signal, this value is maintained during the reception period of the echo signal from a fat layer, then after that reception sensitivity is gradually increased up to 20 dB along the gradient shown in FIG. 3.

The variation aspect of the probe gain in the above-mentioned varied embodiment is also applicable to the above embodiment.

While it is considered to be difficult to fully compensate rate of decrease of the echo signal in a shallow part of a subject by the above-mentioned variation example, the level of the echo signal for inputting to the pre-amplifying unit is drastically improved, whereby enabling the acquisition of an image to facilitate diagnosis of the shallow part of the subject in comparison with conventional apparatuses.

The invention claimed is:

1. An ultrasonic diagnostic apparatus comprising:
an ultrasonic probe including transducers whose sensitivity can be controlled according to a bias voltage, and configured for transmitting ultrasonic waves to a subject to be examined, and for receiving an echo signal from the subject, wherein the transducers of the ultrasonic probe are Capacitive Micromachined Ultrasonic Transducers (cMUT);
a preamplifier for amplifying the echo signal received by the ultrasonic probe;
a time gain control (TGC) amplification means for amplifying the signal output from the preamplifier;
an A/D conversion means for A/D converting the signal output from the TGC amplification means;
an image processing means for constructing an image based on the signal outputted from the A/D conversion means;
a display means for displaying the image constructed by the image processing means; and
a probe gain control means for changing the bias voltage provided to the transducers according to a depth in the subject, said probe gain control means being configured to increase the bias voltage from a shallow depth to a deeper depth than the shallow depth,
wherein the input signal level of the echo signal to the preamplifier is reduced to a voltage which is under or equal to the upper limit of the input range of the preamplifier during a receiving period of the echo at the shallow depth by said probe gain control means, and the input signal level of the echo signal to the preamplifier is increased to the voltage which is under or equal to the upper limit of the input range of the preamplifier during the receiving period of the echo at the deeper depth said probe gain control means.

2. The ultrasonic diagnostic apparatus according to claim 1, wherein the transducers of the ultrasonic probe are electrostrictive elements.

3. The ultrasonic diagnostic apparatus according to claim 1, wherein the shallow depth corresponds to a first predetermined value of the bias voltage, and the deeper depth corresponds to a second predetermined value of the bias voltage.

4. The ultrasonic diagnostic apparatus according to claim 3, wherein the first predetermined value of the bias voltage is smaller than the value upon transmission, and the second predetermined value is larger than the value upon transmission.

5. The ultrasonic diagnostic apparatus according to claim 3, wherein the bias voltage value is maintained, after the passage of predetermined time from reception start time of the echo signal, at the second predetermined value.

6. The ultrasonic diagnostic apparatus according to claim 1, further comprising means for changing a variation aspect of the probe gain dependent on time of the probe gain control means, corresponding to physical attributes of the subject.

7. The ultrasonic diagnostic apparatus according to claim 1, wherein the probe gain control means increases the bias voltage, after decreasing it upon reception time lower than the bias voltage at a transmission time.

8. The ultrasonic diagnostic apparatus according to claim 7, wherein the probe gain control means maintains the bias voltage at a predetermined value after the passage of predetermined time from the reception start time.

9. The ultrasonic diagnostic apparatus according to claim 1, wherein:
sensitivity of the ultrasonic probe is controlled by the bias voltage provided from the probe gain control means,
the input signal level of the echo signal to the preamplifier is increased or decreased to match the bias voltage, and
the input signal level of the echo signal to the preamplifier is increased or decreased in compliance with the sensitivity of ultrasonic probe to match the intensity of the echo signal with the input range of the preamplifier in response to the depth.

10. The ultrasonic diagnostic apparatus according to claim 1, wherein the shallow depth ranges from 0-5 cm, and the deeper depth ranges 5-10 cm.

11. An ultrasonic diagnostic apparatus comprising:
an ultrasonic probe for transmitting ultrasonic waves and for receiving an echo signal, the ultrasonic probe including transducers whose sensitivity can be controlled according to a bias voltage, wherein the transducers of the ultrasonic probe are Capacitive Micromachined Ultrasonic Transducers (cMUT);
a preamplifier for amplifying the echo signal received by the ultrasonic probe;
a time gain control (TGC) amplification means for amplifying the signal output from the preamplifier;
an A/D conversion means for A/D converting the signal output from the TGC amplification means;
an image processing means for constructing an image based on the signal outputted from the A/D conversion means;
a display means for displaying the image constructed by the image processing means; and
a probe gain control means for changing the bias voltage according to a depth in the subject, and matching the intensity of the echo signal with the input range of the preamplifier, said probe gain control means being configured to increase the bias voltage from a shallow depth to a deeper depth than the shallow depth;

wherein the probe gain control means increases the bias voltage from a shallow depth to a deeper depth than the shallow depth so that the input signal level of the echo signal to the preamplifier is reduced to a voltage which is under or equal to the upper limit of the input range of the preamplifier during a receiving period of the echo at the shallow depth by said probe gain control means, and the input signal level of the echo signal to the preamplifier is increased to the voltage which is under or equal to the upper limit of the input range of the preamplifier during the receiving period of the echo at the deeper depth by said probe gain control means.

12. The ultrasonic diagnostic apparatus according to claim 11, wherein the transducers of the ultrasonic probe are electrostriction elements.

13. The ultrasonic diagnostic apparatus according to claim 11, further comprising means for changing a variation aspect of the probe gain dependent on time of the probe gain control means, corresponding to physical attributes of a subject.

14. An ultrasonic diagnostic apparatus comprising:
  an ultrasonic probe for transmitting ultrasonic waves to a subject, and for receiving an echo signal from the subject, the ultrasonic probe including transducers whose sensitivity can be controlled according to a bias voltage, wherein the transducers of the ultrasonic probe are Capacitive Micromachined Ultrasonic Transducers (cMUT);
  a preamplifier for amplifying the echo signal received by the ultrasonic probe;
  a time gain control (TGC) amplification means for amplifying the signal output from the preamplifier;
  an A/D conversion means for ND converting the signal output from the TGC amplification means;
  a time gain variable amplifier for variably changing and amplifying a gain of the signal in time axis direction outputted from the A/D conversion means;
  a digital phasing means for converting the echo signal amplified by the time gain variable amplifier into a digital signal, and performing phasing addition on the echo signal and outputting it;
  an image processing means for constructing an image based on the outputted signal from the digital phasing means;
  a display means for displaying the image constructed by the image processing means;
  a probe gain control means for changing the bias voltage according to a depth in the subject, and matching the intensity of the echo signal with the input range of the preamplifier; and
  a time gain control means for controlling the gain of the time gain variable amplifier to match the echo signal outputted from the preamplifier with an input range of the A/D converter, said probe gain control means being configured to increase the bias voltage from a shallow depth to a deeper depth than the shallow depth;
  wherein the probe gain control means increases the bias voltage from a shallow depth to a deeper depth than the shallow depth so that the input signal level of the echo signal to the preamplifier is reduced to a voltage which is under or equal to the upper limit of the input range of the preamplifier during a receiving period of the echo at the shallow depth by said probe gain control means, and the input signal level of the echo signal to the preamplifier is increased to the voltage which is under or equal to the upper limit of the input range of the preamplifier during the receiving period of the echo at the deeper depth by said probe gain means.

15. The ultrasonic diagnostic apparatus according to claim 14, further comprising overall control means for coordinating and controlling the probe gain control means, the time gain control means and the digital gain control means.

16. The ultrasonic diagnostic apparatus according to claim 14, further comprising means for changing the variation aspect of the gain in compliance with time of the probe gain control means, corresponding to physical attributes of the subject.

17. The ultrasonic diagnostic apparatus according to claim 14, wherein the overall control means starts gain control of time gain control means after the gain of the probe gain control means is fixed at a predetermined value.

* * * * *